United States Patent [19]

Snail et al.

[11] Patent Number: 5,517,315
[45] Date of Patent: May 14, 1996

[54] REFLECTOMETER EMPLOYING AN INTEGRATING SPHERE AND LENS-MIRROR CONCENTRATOR

[75] Inventors: Keith A. Snail, Silver Spring, Md.; Roy Schiff, McLean; David B. Chenault, Alexandria, both of Va.; Leonard M. Hanssen, Gaithersburg, Md.

[73] Assignee: The United States of America as represented by the Secretary of the Navy, Washington, D.C.

[21] Appl. No.: 143,098

[22] Filed: Oct. 29, 1993

[51] Int. Cl.$^6$ ............ G01N 21/55; G01J 1/04; G01B 9/02
[52] U.S. Cl. ............ 356/445; 356/236; 356/346; 356/448
[58] Field of Search ............ 356/346, 445, 356/448, 236

[56] References Cited

U.S. PATENT DOCUMENTS

| | | | |
|---|---|---|---|
| 2,992,588 | 7/1961 | Henderson | 250/228 |
| 3,957,031 | 5/1976 | Winston | 126/270 |
| 4,002,499 | 1/1977 | Winston | 136/126 |
| 4,003,638 | 1/1977 | Winston | 350/293 |
| 4,012,144 | 3/1977 | Hedelman | 356/236 |
| 4,114,592 | 9/1978 | Winston | 126/270 |
| 4,130,107 | 12/1978 | Rabl et al. | 126/270 |
| 4,278,887 | 7/1981 | Lipshutz et al. | 356/236 |
| 4,387,961 | 6/1983 | Winston | 350/296 |
| 4,395,126 | 7/1983 | Kramer | 356/417 |
| 4,640,617 | 2/1987 | Hughes et al. | 356/346 |
| 4,746,214 | 5/1988 | Akiyama et al. | 356/236 |
| 4,815,858 | 3/1989 | Snail | 356/446 |
| 4,922,107 | 5/1990 | Rabl et al. | 250/504 R |
| 4,988,205 | 1/1991 | Snail | 356/446 |
| 5,045,704 | 9/1991 | Coates | 356/445 |
| 5,098,187 | 3/1992 | Judge | 356/236 |
| 5,164,586 | 11/1992 | Hohberg et al. | 356/30 |

OTHER PUBLICATIONS

Snail et al., Integrating Sphere Designs with Isotropic Throughput, App. Opt. vol. 28 No. 10, pp. 1793–1799, May 89.
Gindele et al., Spectral Reflectance Measurements Using an Integrating Sphere in the Infrared, App. Opt. vol. 24 No. 12, pp. 1757–1760, Jun. 85.
Winston et al., Design of Non Imaging Concentrators as Second Staggs in Tandem with Image–Forming First–Stage Concentrators, App. Opt. vol. 19 No. 3, pp. 347–351, Feb. 80.
Collares—Pereira et al., Lens–Mirror Combinations with Maximal Concentration, App. Opt. vol. 16 No. 10, pp. 2677–2683 Oct 77.

*Primary Examiner*—F. L. Evans
*Assistant Examiner*—Robert Kim
*Attorney, Agent, or Firm*—Thomas E. McDonnell; Charles J. Stockstill

[57] ABSTRACT

A reflectometer wherein a light having a predetermined wavelength is projected into an integrating sphere containing a sample whose reflectance is to be measured. As the projected light strikes the sample, rays are reflected back the walls of the integrating sphere; some of which strike the area within the field-of-view of a concentrator. The rays striking within the field-of-view of the concentrator are focused upon a detector element which allows one to determine the reflectance of the sample. A control means is utilized to control the wavelength of the projected light through a spectrophotometer, and calculate the reflectance of the sample.

20 Claims, 2 Drawing Sheets

REFLECTOMETER EMPLOYING AN INTEGRATING SPHERE AND LENS-MIRROR CONCENTRATOR

BACKGROUND OF THE INVENTION

1. Field of the Invention

This invention in general describes a reflectometer and in particular a reflectometer employing an integrating sphere and lens mirror concentrator.

2. Description of Related Art

Integrating spheres are used to measure diffuse reflectance and diffuse transmittance (also known as directional hemispherical reflectance/transmittance). In the visible spectrum, the integrating sphere coatings usually consist of a white diffuser (e.g., MgF, $BASO_4$, or "Halon®"). While for the infrared spectrum, an aluminum surface is frequently sandblasted and then plated with gold.

One of the chief disadvantages of integrating spheres, especially in the infrared spectrum, is that their throughput is low. Low throughputs lead to unacceptable signal-to-noise ratios when measuring samples with low reflectances or transmittances (e.g., <1%). This is also related to the detector field-of-view Recently, in Snail and Hanssen, *Integrating Sphere designs with isotropic throughput,* Appl. Opt. Vol 28, No. 10, May 15. 1989, pp. 1793–1799, a family of three reflectometer designs using nonimaging concentrators to restrict FOV of an integrating sphere's detector, with no concomitant loss in signal, were described. The designs exhibited a uniform throughput over the hemisphere above the sample, but each design had limitations. The first of the described designs is felt to be impractically long for small detector fields-of-view, whereas the second design, which utilized a compound elliptic concentrator (CEC) to view exactly one-half of the sphere, is very sensitive to misalignment errors with specular samples. The third design, which uses an inverted compound parabolic concentrator (CPC), is felt to be impracticable with dewared detectors in the infrared spectrum and also exhibits a nonuniform throughput in the visible light spectrum with a non-dewared detector if the reflectance of the CPC mirror is not sufficiently high (e.g., >95%).

SUMMARY OF THE INVENTION

The object of this invention is to provide a reflectometer that is compact, has a small detector field-of-view and a high, uniform, throughput.

Additional objects, advantages and novel features of the invention will be set forth in part in the description which follows, and in part will become apparent to those skilled in the art upon examination of the following or may be learned by practice of the invention. The objects and advantages may be realized and attained by means of the instrumentalities and combinations particularly pointed out in the appended claims.

According to the present invention, the foregoing and other objects are attained by projecting a light of a predetermined wavelength into an integrating sphere onto a sample whose reflectance is to be measured. As the projected light strikes the sample, rays are reflected off the sample and strike the walls of the integrating sphere where they are again reflected. Some of the reflected rays strike the wall within the field-of-view of a concentrator. The concentrator collects the rays that enter and focuses them upon a detector which measures the amount of reflected light.

A computer controls the wavelength of the light to be projected into the integrating sphere through a spectrophotometer and initially projects the light onto a standard material and then upon the sample whose reflectance is to be measured. The control means determines the measured reflectance of the reference material and computes a calibration factor to be applied to calculate the reflectance of the sample.

DESCRIPTION OF THE PREFERRED EMBODIMENTS

Figure 1:
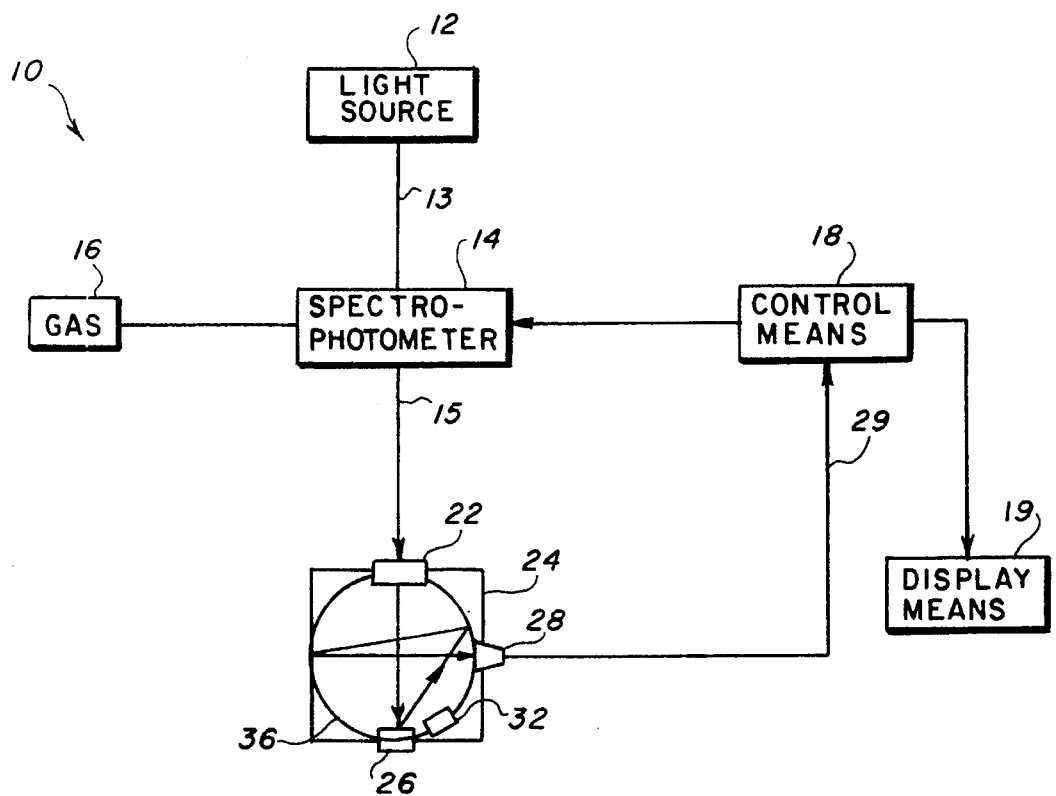
FIG. 1 is a schematic of the reflectometer employing an integrating sphere and a lens mirror concentrator.
Figure 2B:
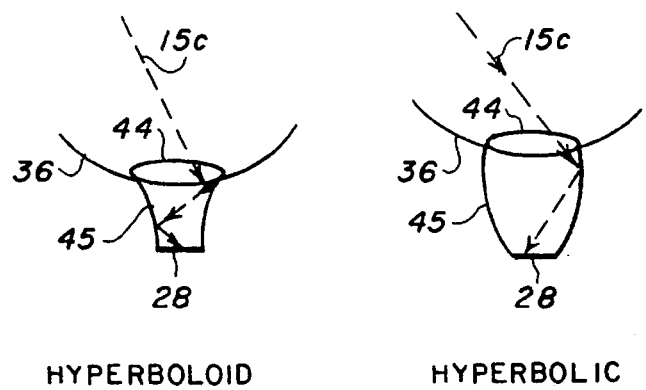
FIG. 2b is a schematic of the detector optics utilizing a hyperbolic concentrator.
Figures 2, 2A:
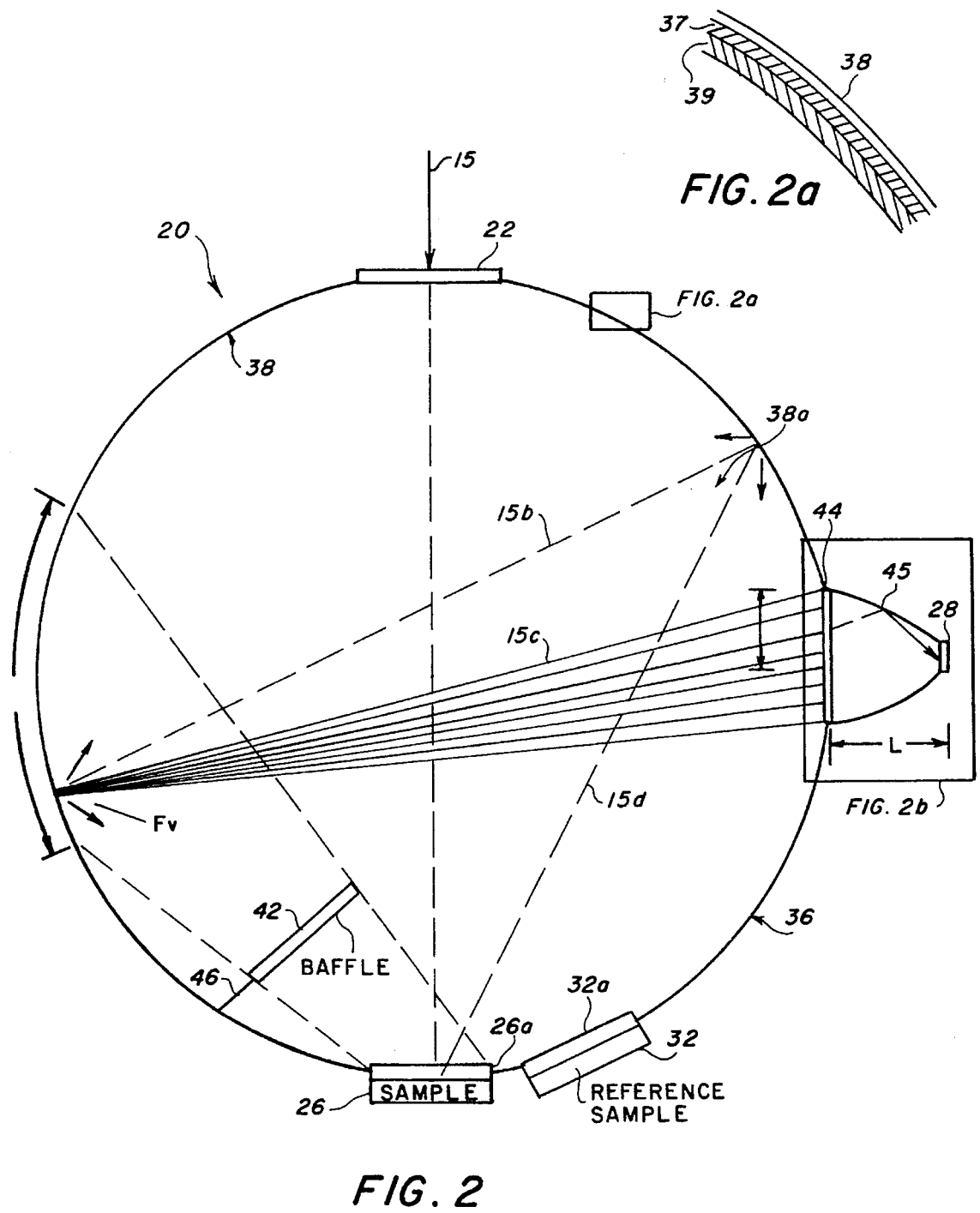
FIG. 2 is a schematic of the integrating sphere with a lens-mirror concentrator.
FIG. 2a is a schematic of a portion of the sphere wall illustrating the layering of the coatings on the sphere wall.

With reference to the drawings in which like numerals represent like elements throughout the views, FIGS. 1, 2 and 2a represent a reflectometer 10 employing an integrating sphere 38 and a lens-mirror concentrator 28.

In the preferred embodiment of the reflectometer 10, FIG. 1, a light source 12 generates a light beam 13, either an infrared (IR) (i.e.,a Nernst Glower or Glow Bar manufactured by Ayers Engineering and Manufacturing Co. of Ramona, Calif.), ultraviolet (UV) (i.e., deuterium lamp) or visible (i.e., Quartz-Halogen lamp), which is projected into a spectrophotometer 14 which measures photometrically the wavelength range of the light beam 13 and radiates a desired wavelength 15 through the port 22 onto a sample 26 whose reflectivity is to be measured by a detector 28 in an integrating sphere 36, such as, a plasma gold-type sphere, such as that manufactured by Labsphere, N. Sutton, N.H.

The spectrophotometer 14 may be either a dispersive type which utilizes a grating that selects one specific wavelength of light to be projected, such as, a 0.25 meter Digikrōm 240, manufactured by CVI Corp. of Tucson Ariz., or an interferometer capable of handling a range of wavelengths, the most common being a Michelsen-type interferometer manufactured by Nicolet of Madison, Wis. The wavelength to be projected onto the sample 26 is selected by a control means 18, such as a computer, which analyzes the signal 29 from the detector 28, stores it within its memory and steps the spectrophotometer 14 to another wavelength to be measured, or in the case of the interferometer, translates the moving mirror. These steps are continued until a predetermined wavelength spread has been measured, whereupon, the control means analyzes the data obtained and displays the analyzed data by a display means 19, i.e., a plotter or visual display, in a form desired by the operator.

Referring to FIG. 2, the beam 15 enters the integrating sphere 36 through the port 22, striking the sample 26 and is reflected back in all directions to the wall of the sphere 38 and into the FOV of the detector 28. A typical path of the reflected light beam 15a strikes the sphere wall 38a and is again reflected in all directions.

The inner surface of a sphere for the visible and near infrared spectrum has a coating 37 of powdered Teflon®-like material, preferably Halon®, with a Lambertian quality For the infrared spectrum, gold (Au) 39, on top of a sandblasted aluminum (Al) or plasma-sprayed Al, is a reflector surface, as shown in FIG. 2a. Surfaces with a Lambertian quality have the directional characteristic of distributing the reflected light uniformly over the entire sphere's inner surface. Therefore, wherever the light reflected from the sample 26 strikes a point on the sphere wall it is evenly distributed over the entire sphere surface. However, the interior of the sphere 36 may be coated with any material that allows for near perfect diffusion in the visible spectrum, e.g., all diffuse coatings, such as barium sulfate ($BASO_4$).

The atmosphere within the integrating sphere 36 should be either a vacuum or an infrared inactive or non-absorbing gas 16, i.e., argon (Ar), oxygen (O), nitrogen (N), etc. The non-absorbing gas 16 is preferred over atmospheres that contain water vapor or carbon dioxide ($CO_2$) and may be injected into the integrating sphere 36 either directly or through the spectrophotometer 14. Such a non-absorbing gas is required in the infrared spectrum since certain absorptive bands will be present in water vapor or $CO_2$ that will produce erroneous reflectivity measurements.

A baffle 42 shields that portion of the sphere wall viewed by a detector 28 from direct reflections from the sample, this area of the sphere 36 having a higher throughput to the detector 28. If the first reflection from the sample 26 were to strike the sphere 36 wall in the area of the field-of-view of the detector 28 then this would provide an erroneous reading of the reflectivity of the sample 26. The portion of the sphere 36 wall shielded from the first reflections off the sample 28 is characterized by the cap radius, F, and forms the field-of-view (FOV) of the detector 28. The baffle is normally elliptical in shape and as thin as possible, preferably (<1 mm thick) and supported from the inner wall of the sphere 38 by a wire 46. However, other shapes such as circles may be utilized. A highly reflective material should coat the baffle 42, preferably one having either a specular (i.e., Au mirror) or diffused (i.e.,sandblasted Al) characteristic. A preferred coating would be the same material used to coat the interior surface of the sphere—a Lambertian material having a bi-directional distribution function (BRDF) of $1/\pi$. The design rules for the placement of the baffle 42 are (1) that it should not be placed so as to enter the beam path of the light 15 entering the sphere 36 and striking the sample 26 and (2) the baffle should not extend into the field-of-view of the detector 28. For a given sphere diameter, beam port 15 size and sample port 26a, there is a maximum field-of-view which still permits the placement of a baffle 42 in a great circle according to these criteria. This is illustrated in FIG. 2. In some instances it may be desirable to have two baffles 42, the first as stated above to shield the sphere wall, F, from reflections emanating from the sample test 26 and a second to shield the sphere wall from reflections emanating from the reference sample 32.

After striking the sphere 36 wall a secondary reflection 15b, is generated which again strikes the sphere wall within the cap radius, F, at point $F_v$, an is again reflected along a path 15c into the concentrator 45 through a port 44. Port 44 is a double convex infrared lens, such as lens manufactured by Janos Technology, Inc. of Townshend, Vt. A low refractive index lens material, such as KCl, is preferred in order to reduce the interface reflectance, thereby broadening the concentrator's acceptance angle. The concentrator-lens 15 may be one of two types utilizing hyperbolic mirrors; a first type is a trumpet-type having a convex hyperbolic mirror. A second type is the compound hyperbolic concentrator (CHC)-type 45 having a concave hyperboloid mirror which provides a one-bounce solution for meridional rays. A meridional ray being a ray that is in a plane containing the optic axis of the concentrator 15. These two types of concentrators are commonly called non-imaging concentrators and both types will provide equally satisfactory results. Under certain conditions, a planar cone is also possible, See, M. Collares-Peireira et al., *Lens-mirror combinations with maximal concentration,* Appl. Opt. Vol. 16, No. 10. pp. 2677–2683. Oct. 1977.

The CHC lens and trumpet-lens restrict the detector's 28 field-of-view (FOV) to the cap radius, F. The non-imaging concentrators are preferably made by the process of diamond turning metal optics, however, they may also be fabricated with an electroforming process such as used by Infrared Laboratories, Tucson, Ariz., and others; all of which will perform satisfactorily.

In the preferred embodiment 20, a CHC type concentrator 45 having a hyperbolic mirror, such as that manufactured by Texas Instruments, Dallas, Tex., is utilized. The reflected light beam 15c passing through the port 44 strikes the concentrator 45 and a reflected meridional ray is projected onto the detector 28. A meridional ray after one reflection within the concentrator 45 strikes the detector 28. However, a second type of ray, the skew ray may also be present. A skew ray is a ray that is not in a plane containing the optic axis of the concentrator 45. With the skew ray there are a multiple of reflections of the beam within the concentrator 45 prior to intercepting the detector 28. The skew rays effect decreases the throughput of the lens-concentrator system slightly near the acceptance angle. The acceptance angle in this embodiment being 10°.

The detector 28, nominally mercury-cadmium-telluride (HgCdTe), for use in the infrared spectrum, such as that manufactured by Belov Technology of New Brunswick, N.J., measures the intensity of the reflected light which is recorded in the control means 18. In the visible light region a photomultiplier tube, such as those manufactured by Hamamatsu Photonics Systems Corp. of Bridgewater, N.J. (e.g., Model R928), or solid state detectors of the silicon photodiode type, such as those manufactured by EG & G of Sunnyvale, Calif., may be selected for use as detectors 28. However, in the near infrared region, from 0.8 microns to about 2.5 microns, a lead sulfide detector element, such as that manufactured by Opto Electronics-Textron of Petaluma, Calif., may be used. However, depending upon the wavelength to be measure, detectors 28 may be made of different materials.

A standard reference material (SRM) 32 is used to calibrate reflectometers in the visible and near infrared spectrums. The light beam 15 entering the sphere 36 through port 22 is directed onto a reference sample 32 which is a material of known reflectivity. The SRM 32 may be either a metal (i.e., gold) of a specular characteristic for the near UV to about 2.5 microns, or ceramic (black or white) material with a diffuse characteristic for use from 300 nm in the UV region to 2–2 ½ microns in the I range. By comparing the standard reflectance of the SAM 32 to the reading of reflectance obtained by the reflectometer 10, a calibration factor for the reflectometer is obtained. (Currently, Sam for wavelengths >2.5 microns are available from the National Physical Laboratory in the United Kingdom.)

A second correction factor may be included in the measured reflectance of the sample 26 to compensate for secondary reflections—those striking the sample 26 and being reflected off it again and striking the cap radius, F, a second time to be measured by the detector 28. This factor can be determined numerically and such computation is well known to those skilled in the art. However, this factor is, in practice, small and it is possible to obtain accurate measurements without this secondary reflection correction factor. A correction for light lost out the beam port 22 can also be made by adding a second detector (not shown) and beam splitter (not shown) in the beam path 15 at the beam port If it is desired, to shrink the cap radius, F, below that determined to be optimum, as shown here, the length of the concentrator (especially compound elliptic concentrators) extends out further and could becomes as long as two sphere diameters. Although this makes a very unwieldy structure, in some circumstances the researcher may feel that this disadvantage is overcome by the results received. Compound Elliptic Concentrators (CEC) tend to be even longer than CHCs.

Currently, the infrared (I) limits of the CHC-lens system will be set by diffraction effects. Typically, as the wavelength of light starts to get comparable to the smaller aperture diameter of the CHC, diffraction effects will start to be noticeable. In the CHC-lens system shown in the preferred embodiment, this limit would be in the mm-wave regime. Practically, the technological limit of measurable wavelength for the infrared region is 25 microns because of the current state-of-the-art of the components of the invention, However, the concept of the invention may be extended to any wavelength, at least 100 microns, with the development of suitable components in the future.

When probing reflectance measurements into the ultraviolet spectrum, the coating of the sphere 38 becomes more critical. In the ultraviolet spectrum, the limits are determined by the reflectivity of the metals coating the inside of the sphere 38. This reflectivity of metals in the UV range tends to fall off very rapidly below 4000 Å. (SEE, F. A. Jenkins & H. E. White, *Fundamentals of Optics*, McGraw-Hill Book Co., New York, N.Y., 1976, pg. 536). Currently, Halon® meets the requirements down to around 200–300 nanometers. The principles set forth on the coupling of the detector 28 set forth in this specification would apply to wavelengths considerably higher in the spectrum and any limitations would depend upon the composition of the coating applied on the sphere 38 interior.

An advantage of the concentrator system is that it has a very high throughput when compared to the existing collimator-based systems (1–50x). Throughput being defined as the ratio of the amount of light that actually makes it to the detector (detector power) to the amount of light that actually enters the sphere (beam power), typically less than one percent. The light entering the sphere has large quantities lost through the beam port and by absorption in the walls of the sphere and the sample. However, the advantages of the integrating sphere far outweigh this low value of throughput which in some cases lowers the signal-to-noise ratio of the reflectometer, a fundamental shortcoming of the integrating sphere.

What is claimed is:

1. A reflectometer for measuring the reflectance of a sample comprising:

a light source for generating a light beam having a plurality of wavelengths;

means for selecting a predetermined wavelength to be projected onto the sample from the plurality of wavelengths generated by the light source;

an integrating sphere;

means for projecting the predetermined wavelength of light onto a sample located within the integrating sphere where it is reflected in a plurality of directions off the sample onto the wall of the integrating sphere where the reflected light is again reflected;

the integrating sphere being further comprised of a detector for measuring the quantum of light reflected off the sample, a non-imaging concentrator having a hyperbolic mirror directing the reflected light from the sample onto the detector and one or more baffles to shield the concentrator from first reflections of the light off of the sample thereby forming a viewable field which is less than the maximum field-of-view of the concentrator;

means for determining the reflectance of the sample based upon a quantum of light reflected off the sample; and means for displaying the reflectance of the sample.

2. A reflectometer, as in claim 1, further comprising a means for controlling the selection of the wavelength to be projected onto the sample, recording, analyzing the reflectance of the sample for presentation on the display means.

3. A reflectometer, as in claim 2, wherein the control means is a computer.

4. A reflectometer, as in claim 1, wherein the light beam is an ultraviolet (UV) light beam.

5. A reflectometer, as in claim 1, wherein the light beam is an infrared (I) light beam.

6. A reflectometer, as in claim 1, wherein the light beam is selected from a group consisting of, an ultraviolet (UV) light and an infrared (IR) light.

7. A reflectometer, as in claim 1, further comprised of a gas medium surrounding the light beam, and a means for drying the gas medium surrounding the light beam.

8. A reflectometer, as in claim 1, wherein the non-imaging concentrator is comprised of a compound hyperbolic concentrator and a lens.

9. A reflectometer, as in claim 1, wherein the means for selecting a predetermined wavelength of light to be projected onto the sample and the means for projecting the predetermined wavelength of light onto the sample is a spectrophotometer.

10. A reflectometer, as in claim 9, wherein the spectrophotometer is a dispersive type.

11. A reflectometer, as in claim 1, wherein the means for selecting a predetermined wavelength of light to be projected onto a sample and the means for projecting the predetermined wavelength of light onto the sample is an interferometer.

12. A reflectometer, as in claim 11, wherein the interferometer is a Michelson-type interferometer.

13. A reflectometer, as in claim 1, further comprising a reference sample for calibrating the reflectometer.

14. A reflectometer, as in claim 1, wherein the display means is a video display.

15. A reflectometer for measuring the reflectance of a sample comprising:

a light source capable of generating a beam of light having a plurality of wavelengths;

means for surrounding the beam of light with a non-absorbing gas to prevent absorption of absorptive bands present in the beam of light by ambient air;

means for transmitting a band of predetermined wavelengths generated by the light source;

means for selecting a plurality of predetermined wavelengths to be projected onto the sample from the predetermined band of wavelengths generated by the light source;

an integrating sphere, which is further comprised of a concentrator and a detector for measuring the beam of light reflected off the sample and one or more baffles to shield the concentrator from first reflections of the beam of light off the sample thereby forming a cap radius, F, or viewable field, which is less than the maximum field-of-view of the concentrator, and means of recording and analyzing the reflected light of the plurality of predetermined wavelengths measured by the concentrator and detector to obtain a total reflectance of the sample and displaying the total reflectance of the sample on a display.

16. A reflectometer, as in claim 15, further comprised of a standard reference material of known reflectivity for calibrating the integrating sphere by comparing a reflectance of the standard reference material to the recorded reflectance obtained by the recording and analyzing means.

17. A method for determining a total reflectance of a sample comprising the steps of:

selecting a wavelength of a light beam to be projected onto a sample located within an integrating sphere whose reflectivity is to be determined;

projecting the light into the integrating sphere through a spectrophotometer onto the sample;

collecting a reflected light from the sample and the walls of the integrating sphere projected onto a cap radius, F, of the integrating sphere with a concentrator having a predetermined field-of-view;

measuring the reflected light collected by the concentrator to ascertain a reflectance of the sample at the preselected wavelength;

repeating the step of selecting the wavelength of the light to be projected into the integrating sphere by varying the preselected wavelength over a predetermined plurality of wavelengths;

analyze the plurality of reflectivity measurements to obtain the total reflectance of the sample for the predetermined plurality of wavelengths;

projecting a light beam through the spectrophotometer onto a standard reference material inside the integrating sphere and obtain a calibration factor for the integrating sphere by comparing the standard reflectance of the standard reference material to the reading of a calibration reflectance;

correct the total reflectivity by applying the correction factor; and display the corrected total reflectance of the sample on a display.

18. A method, as in claim 17, further comprising the step of drying the gas surrounding the light beam prior to projecting the light beam into the integrating sphere to prevent absorption of the light beam by absorptive bands in the surrounding gas.

19. A method for determining the reflectance of a sample, as in claim 17, wherein the concentrator is comprised of a compound hyperbolic concentrator and a lens.

20. A method for determining the reflectance of a sample, as in claim 17, wherein the concentrator is comprised of a trumpet-type concentrator and a lens.

* * * * *